(12) United States Patent
Li et al.

(10) Patent No.: US 7,838,026 B2
(45) Date of Patent: Nov. 23, 2010

(54) BURST-RELEASE POLYMER COMPOSITION AND DOSAGE FORMS COMPRISING THE SAME

(75) Inventors: Shun-Por Li, Lansdale, PA (US); Der-Yang Lee, Flemington, NJ (US); Frank J. Bunick, Randolph, NJ (US); Jen Chi Chen, Morrisville, PA (US); Harry S. Sowden, Glenside, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 1082 days.

(21) Appl. No.: 10/695,347

(22) Filed: Oct. 28, 2003

(65) Prior Publication Data

US 2004/0129174 A1 Jul. 8, 2004

Related U.S. Application Data

(63) Continuation-in-part of application No. 10/393,765, filed on Mar. 21, 2003, now abandoned, which is a continuation-in-part of application No. PCT/US02/31129, filed on Sep. 28, 2002, and a continuation-in-part of application No. PCT/US02/31117, filed on Sep. 28, 2002, and a continuation-in-part of application No. PCT/US02/31062, filed on Sep. 28, 2002, and a continuation-in-part of application No. PCT/US02/31024, filed on Sep. 28, 2002, and a continuation-in-part of application No. PCT/US02/31163, filed on Sep. 28, 2002, which is a continuation-in-part of application No. 09/966,939, filed on Sep. 28, 2001, now Pat. No. 6,837,696, which is a continuation-in-part of application No. 09/966,509, filed on Sep. 28, 2001, now Pat. No. 6,767,200, which is a continuation-in-part of application No. 09/966,497, filed on Sep. 28, 2001, now Pat. No. 7,122,143, which is a continuation-in-part of application No. 09/967,414, filed on Sep. 28, 2001, now Pat. No. 6,742,646, and a continuation-in-part of application No. 09/966,450, filed on Sep. 28, 2001, now Pat. No. 6,982,094.

(51) Int. Cl.
A61K 9/20 (2006.01)
A61K 9/30 (2006.01)
A61K 9/32 (2006.01)
A61K 9/48 (2006.01)
A61K 9/56 (2006.01)

(52) U.S. Cl. .................. 424/451; 424/452; 424/457; 424/463; 424/464; 424/465; 424/468; 424/480

(58) Field of Classification Search .......... 424/451–502
See application file for complete search history.

(56) References Cited

U.S. PATENT DOCUMENTS

| 545,832 A | 9/1895 | Turnbull |
|---|---|---|
| 582,438 A | 5/1897 | Scheidler |
| 599,865 A | 3/1898 | Richards |
| 1,036,647 A | 8/1912 | Komarek |
| 1,437,816 A | 12/1922 | Paine et al. |
| 1,900,012 A | 3/1933 | Ernst |
| 2,307,371 A | 1/1943 | Hileman |
| 2,415,997 A | 2/1947 | Eldred |
| 2,823,789 A | 2/1958 | Henning |
| 2,849,965 A | 9/1958 | Stott |
| 2,931,276 A | 4/1960 | Zerlin |
| 2,946,298 A | 7/1960 | Doepel et al. |
| 2,963,993 A | 12/1960 | Stott |
| 2,966,431 A | 12/1960 | Lorenz et al. |
| 3,029,752 A | 4/1962 | Frank |
| 3,085,942 A | 4/1963 | Magid et al. |
| 3,096,248 A | 7/1963 | Rudzki |
| 3,108,046 A | 10/1963 | Harbit |
| 3,146,169 A | 8/1964 | Stephenson et al. |
| 3,177,280 A | 4/1965 | Ford et al. |
| 3,185,626 A | 5/1965 | Baker |
| 3,279,360 A | 10/1966 | Smith et al. |
| 3,300,063 A | 1/1967 | Jensen et al. |
| 3,330,400 A | 7/1967 | Alexander |
| 3,371,136 A | 2/1968 | Johannsen |
| 3,430,535 A | 3/1969 | Campbell |
| 3,432,592 A | 3/1969 | Speiser |
| 3,458,968 A | 8/1969 | Gregory, Jr. |

(Continued)

FOREIGN PATENT DOCUMENTS

CN 1092641 A 9/1994

(Continued)

OTHER PUBLICATIONS

J.C. Carter Pharmaceutical Canada 2003, 4(1).*

(Continued)

Primary Examiner—Rebecca L Anderson
Assistant Examiner—Jason M Nolan
(74) Attorney, Agent, or Firm—Laura A. Donnelly

(57) ABSTRACT

A composition comprising a high molecular weight, water soluble polymer having a cloud point from about 20 to about 90° C. and at least one carrageenan is provided. The composition may be used as a component of a pharmaceutical dosage form, such as the shell of a dosage form, to provide burst release of active ingredient contained therein.

12 Claims, 2 Drawing Sheets

U.S. PATENT DOCUMENTS

| | | |
|---|---|---|
| 3,555,608 A | 1/1971 | Maekawa et al. |
| 3,563,170 A | 2/1971 | Cvacho et al. |
| 3,567,043 A | 3/1971 | Sirvet et al. |
| 3,584,114 A | 6/1971 | Cavalli et al. |
| 3,605,479 A | 9/1971 | Bradlee |
| 3,627,583 A | 12/1971 | Troy et al. |
| 3,656,518 A | 4/1972 | Aronson |
| 3,726,622 A | 4/1973 | De Troyer et al. |
| 3,804,570 A | 4/1974 | Hoschele et al. |
| 3,811,552 A | 5/1974 | Wagers et al. |
| 3,832,252 A | 8/1974 | Higuchi et al. |
| 3,851,751 A | 12/1974 | Jones |
| 3,884,143 A | 5/1975 | Ackley |
| 3,891,375 A | 6/1975 | Pilewski et al. |
| 3,912,441 A | 10/1975 | Shimada et al. |
| 3,975,888 A | 8/1976 | Jones |
| 4,076,819 A | 2/1978 | Maffrand |
| 4,097,606 A | 6/1978 | Chavkin et al. |
| 4,139,589 A | 2/1979 | Beringer et al. |
| 4,173,626 A | 11/1979 | Dempski et al. |
| 4,230,693 A | 10/1980 | Izzo et al. |
| 4,268,243 A | 5/1981 | Koshkin et al. |
| 4,271,142 A | 6/1981 | Puglia et al. |
| 4,271,206 A | 6/1981 | Fariel et al. |
| 4,273,793 A | 6/1981 | Fariel et al. |
| 4,279,926 A | 7/1981 | Bruzzese et al. |
| 4,292,017 A | 9/1981 | Doepel |
| 4,327,076 A | 4/1982 | Puglia et al. |
| 4,362,757 A | 12/1982 | Chen et al. |
| 4,371,516 A | 2/1983 | Gregory et al. |
| 4,372,942 A | 2/1983 | Cimiluca |
| 4,392,493 A | 7/1983 | Niemeijer |
| 4,413,709 A | 11/1983 | Kazumi |
| 4,425,332 A | 1/1984 | James |
| 4,449,983 A | 5/1984 | Cortese et al. |
| 4,473,526 A | 9/1984 | Buhler et al. |
| 4,518,335 A | 5/1985 | Pujari |
| 4,528,335 A | 7/1985 | Selby et al. |
| 4,533,345 A | 8/1985 | Louw |
| 4,543,370 A | 9/1985 | Porter et al. |
| 4,544,345 A | 10/1985 | Buhler et al. |
| 4,569,650 A | 2/1986 | Kramer |
| 4,576,604 A | 3/1986 | Guittard et al. |
| 4,643,894 A | 2/1987 | Porter et al. |
| 4,661,521 A | 4/1987 | Salpekar et al. |
| 4,665,116 A | 5/1987 | Kornhaber et al. |
| 4,683,256 A | 7/1987 | Porter et al. |
| 4,684,534 A | 8/1987 | Valentine |
| 4,686,212 A | 8/1987 | Ducatman et al. |
| 4,724,150 A | 2/1988 | Knebl et al. |
| 4,725,441 A | 2/1988 | Porter et al. |
| 4,744,741 A | 5/1988 | Glover et al. |
| 4,749,575 A | 6/1988 | Rotman |
| 4,757,090 A | 7/1988 | Salpekar et al. |
| 4,762,719 A | 8/1988 | Forester |
| 4,781,714 A | 11/1988 | Eckenhoff et al. |
| 4,801,461 A | 1/1989 | Hamel et al. |
| 4,802,924 A | 2/1989 | Woznicki et al. |
| 4,808,413 A * | 2/1989 | Joshi et al. .................. 424/458 |
| 4,813,818 A | 3/1989 | Sanzone |
| 4,820,524 A | 4/1989 | Berta |
| 4,828,841 A | 5/1989 | Porter et al. |
| 4,828,845 A | 5/1989 | Zamudio-Tena et al. |
| 4,851,226 A | 7/1989 | Julian et al. |
| 4,853,249 A | 8/1989 | Takashima et al. |
| 4,857,330 A | 8/1989 | Stephens et al. |
| 4,863,742 A | 9/1989 | Panoz et al. |
| 4,865,849 A | 9/1989 | Conte et al. |
| 4,873,231 A | 10/1989 | Smith |
| 4,882,167 A | 11/1989 | Jang |
| 4,894,234 A | 1/1990 | Sharma et al. |
| 4,894,236 A | 1/1990 | Jang et al. |
| 4,898,733 A | 2/1990 | DePrince et al. |
| 4,906,478 A | 3/1990 | Valentine et al. |
| 4,929,446 A | 5/1990 | Bartolucci |
| 4,936,440 A | 6/1990 | Focke et al. |
| 4,943,227 A | 7/1990 | Facchini |
| 4,965,027 A | 10/1990 | Takahashi |
| 4,980,169 A | 12/1990 | Oppenheimer et al. |
| 4,980,170 A | 12/1990 | Schneider et al. |
| 4,984,240 A | 1/1991 | Keren-Zvi et al. |
| 4,992,277 A * | 2/1991 | Sangekar et al. ............ 424/465 |
| 4,996,061 A | 2/1991 | Webb et al. |
| 5,002,970 A | 3/1991 | Eby, III |
| 5,006,297 A | 4/1991 | Brown et al. |
| 5,030,447 A | 7/1991 | Joshi et al. |
| 5,059,112 A | 10/1991 | Wieser |
| 5,073,379 A | 12/1991 | Klimesch et al. |
| 5,075,114 A | 12/1991 | Roche |
| 5,088,915 A | 2/1992 | Korsch et al. |
| 5,089,270 A | 2/1992 | Hampton et al. |
| 5,098,715 A | 3/1992 | McCabe et al. |
| 5,100,675 A | 3/1992 | Cho et al. |
| 5,145,868 A | 9/1992 | von Sprecher et al. |
| 5,146,730 A | 9/1992 | Sadek et al. |
| 5,154,278 A | 10/1992 | Deutsch |
| 5,158,728 A | 10/1992 | Sanderson et al. |
| 5,169,645 A | 12/1992 | Shukla et al. |
| 5,178,878 A | 1/1993 | Wehling et al. |
| 5,188,840 A | 2/1993 | Iida et al. |
| 5,190,927 A * | 3/1993 | Chang et al. .................. 514/54 |
| 5,200,191 A | 4/1993 | Steele et al. |
| 5,213,738 A | 5/1993 | Hampton et al. |
| 5,213,808 A | 5/1993 | Bar-Shalom et al. |
| 5,223,264 A | 6/1993 | Wehling et al. |
| 5,228,916 A | 7/1993 | Berta |
| 5,229,164 A | 7/1993 | Pins et al. |
| 5,234,099 A | 8/1993 | Berta |
| 5,267,577 A | 12/1993 | Rizzoli et al. |
| 5,274,162 A | 12/1993 | Glazier |
| 5,275,822 A | 1/1994 | Valentine et al. |
| 5,286,497 A | 2/1994 | Hendrickson et al. |
| 5,341,248 A | 8/1994 | Amada et al. |
| 5,342,626 A | 8/1994 | Winston, Jr. et al. |
| 5,350,548 A | 9/1994 | Hinzpeter et al. |
| 5,362,508 A | 11/1994 | Wheeler et al. |
| 5,368,863 A | 11/1994 | Eckenhoff et al. |
| 5,391,378 A | 2/1995 | Sanderson |
| 5,405,642 A | 4/1995 | Gilis et al. |
| 5,415,868 A | 5/1995 | Smith et al. |
| 5,421,447 A | 6/1995 | Ruth et al. |
| 5,424,075 A | 6/1995 | Daher et al. |
| 5,427,614 A | 6/1995 | Wittwer et al. |
| 5,429,226 A | 7/1995 | Ensch et al. |
| 5,429,484 A | 7/1995 | Honda et al. |
| 5,436,026 A | 7/1995 | Berta |
| 5,456,563 A | 10/1995 | Halbo |
| 5,456,920 A | 10/1995 | Matoba et al. |
| 5,459,983 A | 10/1995 | Sadek et al. |
| 5,464,631 A | 11/1995 | Hoover et al. |
| 5,464,632 A | 11/1995 | Cousin et al. |
| 5,464,633 A | 11/1995 | Conte et al. |
| 5,489,436 A | 2/1996 | Hoy et al. |
| 5,494,681 A | 2/1996 | Cuca et al. |
| 5,500,227 A | 3/1996 | Oshlack et al. |
| 5,510,385 A | 4/1996 | Stroppolo et al. |
| 5,511,361 A | 4/1996 | Sauter |
| 5,525,179 A | 6/1996 | Stickling |
| 5,538,125 A | 7/1996 | Berta |
| 5,558,879 A | 9/1996 | Chen et al. |
| 5,578,316 A | 11/1996 | Bhardwaj et al. |
| 5,578,336 A | 11/1996 | Monte |
| 5,607,045 A | 3/1997 | Kronseder |
| 5,609,010 A | 3/1997 | Sauter |

| | | | | | | |
|---|---|---|---|---|---|---|
| 5,614,207 | A | 3/1997 | Shah et al. | 6,395,298 B1 | 5/2002 | Flanagan et al. |
| 5,626,896 | A | 5/1997 | Moore et al. | 6,405,853 B1 | 6/2002 | Cook et al. |
| 5,630,871 | A | 5/1997 | Jordan | 6,423,256 B1 | 7/2002 | Kothrade et al. |
| 5,643,984 | A | 7/1997 | Mueller et al. | 6,433,015 B1 | 8/2002 | Meyer |
| 5,648,033 | A | 7/1997 | Bogue et al. | 6,499,984 B1 | 12/2002 | Ghebre-Sellassie et al. |
| 5,656,296 | A | 8/1997 | Khan et al. | 6,558,722 B2 | 5/2003 | Corriveau et al. |
| 5,658,589 | A | 8/1997 | Parekh et al. | 6,669,883 B1 | 12/2003 | Rosenberg et al. |
| 5,672,364 | A | 9/1997 | Kato et al. | 6,727,213 B2 | 4/2004 | Waschenbach et al. |
| 5,679,406 | A | 10/1997 | Berta | 6,730,646 B1 | 5/2004 | Waschenbach et al. |
| 5,681,583 | A | 10/1997 | Conte et al. | 6,737,005 B1 | 5/2004 | Rosenberg et al. |
| 5,681,584 | A | 10/1997 | Savastano et al. | 6,742,646 B2 | 6/2004 | Sowden et al. |
| 5,711,961 | A | 1/1998 | Reiner et al. | 6,837,696 B2 | 1/2005 | Sowden et al. |
| 5,738,874 | A | 4/1998 | Conte et al. | 6,880,694 B2 | 4/2005 | Sowden |
| 5,743,377 | A | 4/1998 | Kronseder | 6,913,766 B1 | 7/2005 | Krumme et al. |
| 5,756,123 | A * | 5/1998 | Yamamoto et al. ........ 424/451 | 6,991,808 B2 | 1/2006 | Brubaker et al. |
| 5,782,337 | A | 7/1998 | Langland | 7,182,199 B2 | 2/2007 | Sowden et al. |
| 5,795,588 | A | 8/1998 | Sauter | 7,217,381 B2 | 5/2007 | Sowden |
| 5,807,579 | A | 9/1998 | Vilkov et al. | 7,297,345 B2 | 11/2007 | Sowden |
| 5,813,513 | A | 9/1998 | Taube | 7,323,192 B2 | 1/2008 | Luber et al. |
| 5,824,338 | A | 10/1998 | Jacobs et al. | 2001/0001280 A1 | 5/2001 | Dong et al. |
| 5,827,548 | A | 10/1998 | Lavallee et al. | 2001/0024678 A1 | 9/2001 | Scott et al. |
| 5,827,563 | A | 10/1998 | Battist et al. | 2002/0012675 A1* | 1/2002 | Jain et al. .................. 424/400 |
| 5,827,874 | A | 10/1998 | Meyer et al. | 2002/0028240 A1 | 3/2002 | Sawada et al. |
| 5,830,501 | A | 11/1998 | Dong et al. | 2002/0082299 A1 | 6/2002 | Meyer |
| 5,830,502 | A | 11/1998 | Dong et al. | 2002/0187190 A1 | 12/2002 | Cade et al. |
| 5,834,035 | A | 11/1998 | Osada et al. | 2003/0015814 A1 | 1/2003 | Krull et al. |
| 5,837,301 | A | 11/1998 | Arnott et al. | 2003/0068367 A1 | 4/2003 | Sowden et al. |
| 5,840,334 | A * | 11/1998 | Raiden et al. ............... 424/464 | 2003/0072799 A1 | 4/2003 | Sowden et al. |
| 5,853,760 | A | 12/1998 | Cremer | 2003/0086973 A1 | 5/2003 | Sowden et al. |
| 5,871,079 | A | 2/1999 | Nannini et al. | 2003/0124183 A1 | 7/2003 | Sowden et al. |
| 5,871,781 | A | 2/1999 | Myers et al. | 2003/0203016 A1 | 10/2003 | Suwelack |
| 5,879,728 | A | 3/1999 | Graff et al. | 2003/0224043 A1 | 12/2003 | Appel et al. |
| 5,897,910 | A | 4/1999 | Rosenberg et al. | 2004/0129174 A1 | 7/2004 | Li et al. |
| 5,912,013 | A | 6/1999 | Rudnic et al. | 2004/0166080 A1 | 8/2004 | Assmus et al. |
| 5,922,352 | A * | 7/1999 | Chen et al. ................. 424/465 | 2005/0008696 A1 | 1/2005 | Sowden et al. |
| 5,942,034 | A | 8/1999 | Brehant et al. | 2005/0147677 A1 | 7/2005 | Sowden |
| 5,962,053 | A | 10/1999 | Merritt, II | | | |
| 5,996,768 | A | 12/1999 | Boyce et al. | | | |

FOREIGN PATENT DOCUMENTS

| | | |
|---|---|---|
| CN | 1137926 A | 12/1996 |
| DE | 7535875 U | 3/1976 |
| DE | 2710307 | 9/1977 |
| DE | 2752971 A | 6/1979 |
| DE | 4025487 A | 2/1992 |
| DE | 19834180 A1 | 2/2000 |
| DE | 19954420 A1 | 5/2001 |
| DE | 19963569 A1 | 7/2001 |
| EP | 0234670 A | 9/1987 |
| EP | 0279682 A | 8/1988 |
| EP | 0320320 A | 6/1989 |
| EP | 0088556 B1 | 9/1989 |
| EP | 0387885 B1 | 9/1990 |
| EP | 0239983 B1 | 11/1991 |
| EP | 0455599 A1 | 11/1991 |
| EP | 0294993 B1 | 12/1991 |
| EP | 0481547 A1 | 4/1992 |
| EP | 0531524 B1 | 3/1993 |
| EP | 0572731 A1 | 12/1993 |
| EP | 0610854 A | 8/1994 |
| EP | 0611032 A1 | 9/1994 |
| EP | 0619854 B1 | 10/1994 |
| EP | 0622408 A | 11/1994 |
| EP | 0646650 A2 | 4/1995 |
| EP | 0646650 A3 | 4/1995 |
| EP | 0740938 B1 | 11/1996 |
| EP | 0771533 B1 | 5/1997 |
| EP | 0771533 B1 | 7/1997 |
| EP | 0788790 A2 | 8/1997 |
| EP | 0834516 B1 | 4/1998 |
| EP | 0861659 A1 | 9/1998 |
| EP | 0864324 A | 9/1998 |
| EP | 0875245 A | 11/1998 |
| EP | 0963836 A1 | 12/1999 |

| | | | |
|---|---|---|---|
| 5,997,905 | A | 12/1999 | McTeigue et al. |
| 6,001,391 | A | 12/1999 | Zeidler et al. |
| 6,099,859 | A | 8/2000 | Cheng et al. |
| 6,103,257 | A | 8/2000 | Nisonoff |
| 6,103,260 | A | 8/2000 | Luber et al. |
| 6,117,479 | A | 9/2000 | Hogan et al. |
| 6,120,802 | A | 9/2000 | Breitenbach et al. |
| 6,126,877 | A | 10/2000 | Gille et al. |
| 6,149,939 | A | 11/2000 | Strumor et al. |
| 6,149,943 | A | 11/2000 | McTeigue et al. |
| 6,177,125 | B1 | 1/2001 | Voss |
| 6,183,681 | B1 | 2/2001 | Sullivan et al. |
| 6,194,000 | B1 | 2/2001 | Smith et al. |
| 6,200,590 | B1 | 3/2001 | Eley |
| 6,210,710 | B1 | 4/2001 | Skinner |
| 6,213,283 | B1 | 4/2001 | Bailey et al. |
| 6,217,903 | B1 | 4/2001 | Skinner |
| 6,217,907 | B1 | 4/2001 | Hunter et al. |
| 6,227,836 | B1 | 5/2001 | Kato et al. |
| 6,234,300 | B1 | 5/2001 | De Vos et al. |
| 6,245,356 | B1 | 6/2001 | Baichwal |
| 6,248,760 | B1 | 6/2001 | Wilhelmsen |
| 6,264,985 | B1 | 7/2001 | Cremer |
| 6,270,790 | B1 | 8/2001 | Robinson et al. |
| 6,270,805 | B1 | 8/2001 | Chen et al. |
| 6,272,446 | B1 | 8/2001 | Baekke et al. |
| 6,274,162 | B1 | 8/2001 | Steffenino et al. |
| 6,276,917 | B1 | 8/2001 | Gutierrez et al. |
| 6,322,819 | B1 | 11/2001 | Burnside et al. |
| 6,326,028 | B1 | 12/2001 | Nivaggioli et al. |
| 6,350,398 | B1 | 2/2002 | Breitenbach et al. |
| 6,358,525 | B1 | 3/2002 | Guo et al. |
| 6,365,185 | B1 | 4/2002 | Ritschel et al. |
| 6,372,254 | B1 | 4/2002 | Ting et al. |
| 6,394,094 | B1 | 5/2002 | McKenna et al. |

| | | | |
|---|---|---|---|
| EP | 1029892 | | 8/2000 |
| EP | 1077065 | A1 | 2/2001 |
| EP | 0950402 | B1 | 5/2003 |
| FR | 1603314 | A6 | 4/1971 |
| FR | 2604904 | | 4/1988 |
| GB | 759081 | A | 10/1956 |
| GB | 866681 | A | 4/1961 |
| GB | 888038 | | 1/1962 |
| GB | 936386 | | 9/1963 |
| GB | 994742 | | 6/1965 |
| GB | 1144915 | | 3/1969 |
| GB | 1227837 | A | 4/1971 |
| GB | 1235926 | A | 6/1971 |
| GB | 1372040 | | 10/1974 |
| GB | 1510772 | | 5/1978 |
| GB | 2182559 | A | 5/1987 |
| GB | 2197778 | A | 6/1988 |
| GB | 2284760 | A | 6/1995 |
| JP | 37-2644 | | 1/1960 |
| JP | 03261719 | A | 11/1991 |
| JP | 04008288 | | 1/1992 |
| JP | 07-116228 | | 1/1994 |
| JP | 08245372 | A | 9/1996 |
| JP | 2001-072579 | | 3/2001 |
| JP | 2002-95426 | A | 4/2002 |
| NL | 8602556 | | 5/1998 |
| WO | WO 93/13758 | | 7/1993 |
| WO | WO 94/06416 | A1 | 3/1994 |
| WO | WO 94/07470 | A1 | 4/1994 |
| WO | WO 95/02396 | A1 | 1/1995 |
| WO | WO 95/15156 | A1 | 6/1995 |
| WO | WO 96/07401 | A | 3/1996 |
| WO | WO 97/06695 | A1 | 2/1997 |
| WO | WO 97/15293 | A2 | 5/1997 |
| WO | WO 98/20870 | A1 | 5/1998 |
| WO | WO 99/00122 | A1 | 1/1999 |
| WO | WO 99/02136 | A1 | 1/1999 |
| WO | WO 99/20745 | | 4/1999 |
| WO | WO 9920745 | * | 4/1999 |
| WO | WO 99/22769 | A1 | 5/1999 |
| WO | WO 99/32092 | A1 | 7/1999 |
| WO | WO 99/51209 | A1 | 10/1999 |
| WO | WO 99/56730 | A1 | 11/1999 |
| WO | WO 99/62496 | A1 | 12/1999 |
| WO | WO 00/18447 | A2 | 4/2000 |
| WO | WO 00/18447 | A3 | 4/2000 |
| WO | WO 00/25755 | A1 | 5/2000 |
| WO | WO 00/40223 | | 7/2000 |
| WO | WO 00/61110 | | 10/2000 |
| WO | WO 01/00179 | | 1/2001 |
| WO | WO 01/15889 | A1 | 3/2001 |
| WO | WO 01/21155 | A1 | 3/2001 |
| WO | 01/26633 | A1 | 4/2001 |
| WO | WO 01/26634 | A1 | 4/2001 |
| WO | WO 01/32150 | A1 | 5/2001 |
| WO | WO 01/43943 | A | 6/2001 |
| WO | WO 01/56550 | A1 | 8/2001 |
| WO | WO 02/19833 | A2 | 3/2002 |
| WO | WO 02/19833 | A3 | 3/2002 |
| WO | WO 03/000293 | A | 1/2003 |
| WO | WO 03/020246 | A1 | 3/2003 |
| WO | WO 03/028619 | A2 | 4/2003 |

OTHER PUBLICATIONS

J.C. Carter Pharmaceutical Canada 2001, 2(3).*
R.H. Dave, Drug Topics: Overview of pharmaceutical excipients used in tablets and capsules, Oct. 28, 2008, downloaded from the internet Jun. 9, 2009.*
Banker et al. Chapter 11 in The Theory and Practice of Industrial Pharmacy Lea & Febiger (pub.) Lachman et al. (ed.) 1986, pp. 293-345.*
J.C. Carter Pharmaceutical Canada 2001, 1(3).*
007034092—Abstract Derwent WPI5/1/2001.
Leiberman, et al., *Pharmaceutical Dosage Forms*—Tablets, 1990, pp. 213-217, 327-329, vol. 2, $2^{nd}$ ed., Marcel Dekker, Inc.
Elizabeth Carbide Die Co., Inc., *The Elizabeth Companies Tablet Design Training Manual*, p. 7.
Lachman, et al., *The Theory and Practice of Industrial Pharmacy*, 1986, Chapter 11, $3^{rd}$ ed.
International Search Report re: PCT/US2004/035763 dated Nov. 10, 2005.
PCT Search Report for PCT/US02/30614 dated Feb 26, 2003.
PCT Search Report for PCT/US02/30570 dated Dec. 16, 2002.
PCT Search Report for PCT/US02/30613 dated Mar. 17, 2003.
PCT Search Report for PCT/US02/31117 dated Mar. 3, 2003.
PCT Search Report for PCT/US02/31062 dated Apr. 28, 2003.
PCT Search Report for PCT/US02/31024 dated Feb. 26, 2003.
PCT Search Report for PCT/US02/31163 dated Feb. 20, 2003.
PCT Search Report for PCT/US02/31129 dated Mar. 13, 2003.
PCT Search Report for PCT/US03/08859 dated Aug. 22, 2003.
D'Arcy et al. International Journal of Pharmaceutics vol. 88(1992) 285-291.
Daoudal, J.; "Appetising tablet for domestic animals . . . "; "Tablet for domestic animal" EP0320320A2; Jun. 14, 1999; Derwent World Patents Index, Dialog File No. 351 Accession No. 7909478; Derwent Information Ltd. Abstract.
Eith, L., et al., "Injection-Moulded Drug-Delivery Systems", Manufacturing Chemist (Jan. 1987), pp. 21-25.
C. De Brabander et al., "Matrix mini-tablets based on starch/microcrystalline wax mixtures" International Journal of Pharmaceutics, Netherlands Apr. 20, 2000, vol. 199, No. 2, pp. 195-203 XP002233674.
Catellani et al. Internation Journal of Pharmaceutics vol. 88(1992) 285-291 "Centrifugal die filling system in a new rotary tablet machine."
Cuff & Rauf Pharm Tech Jun. 1998 96-106 "A Preliminary Evaluation of Injection Molding as a Technology to Produce Tablets."
Grove, R. "Tips for Chocolate Liqueur Cherries", Candy Industry, Nov. 1994, p. 23.
Hawleys Condensed Chemical Dictionary, 12th Edition, 1993, pp. 960-921.
http://www.espi-metals.com/tech/mesh.htm: accessed May 14, 2009.
Patent Abstracts of Japan vol. 012, No. 091 (M-679) Mar. 24, 1988 & JP62230600A (Kyowa Hakko Kogyo Co Ltd.) Oct. 9, 1987 abstract.
Patent Abstracts of Japan vol. 007, No. 050(M-197) Feb. 26, 1983 & JP 0617096A (Yoshitsuka Seikl:KK) Dec. 8, 1982 abstract.
Patent Abstracts of Japan vol. 018, No. 514 (M-1680) Sep. 28, 1994 & JP 0617096A (Kao Corp) Jun. 28, 1994 abstract.
Repin J.A. et al; "Injection moulding machine for mass production . . . " "Jet moulding machine for products from thermoplastic polymer materials" DE2752971A1; Jun. 7, 1979; Drewent World Patents Index; Dialog File No.
Rosato, Domminick & Donald, "Injection Molding Handbook", The Complete Molding Operation Technology, Performance, Economics (1986), pp. 189-191 &794-795.
Websters II, New College Dictionary p. 691, 1995.
Translation of Japanese Examiners Notification of Reasons for Refusal.
Uhlherr, PHT, et al., "Static Measurement of Yield Stress Using a Cylindrical Penetrometer," Korea-Australia Rheology, Journal, vol. 14, No. 1, Mar. 2002, pp. 17-23.

* cited by examiner

US 7,838,026 B2

BURST-RELEASE POLYMER COMPOSITION AND DOSAGE FORMS COMPRISING THE SAME

CROSS-REFERENCE TO RELATED APPLICATIONS

This application is a continuation-in-part of Ser. No. 10/393,765 filed on Mar. 21, 2003, now abandoned which in turn is a continuation-in-part of PCT Application Nos. PCT/US02/31129, filed Sep. 28, 2002; PCT/US02/31117, filed Sep. 28, 2002; PCT/US02/31062, filed Sep. 28, 2002; PCT/US02/31024, filed Sep. 28, 2002; and PCT/US02/31163, filed Sep. 28, 2002, which are each continuations-in-part of U.S. Ser. No. 09/966,939, filed Sep. 28, 2001 now U.S. Pat. No. 6,837,696; U.S. Ser. No. 09/966,509, filed Sep. 28, 2001 now U.S. Pat. No. 6,767,200; U.S. Ser. No. 09/966,497, filed Sep. 28, 2001; now U.S. Pat. No.7,122,143 U.S. Ser. No. 09/967,414, filed Sep. 28, 2001 now U.S. Pat. No. 6,742,646; and U.S. Ser. No. 09/966,450, filed Sep. 28, 2001, now U.S. Pat. No. 6,982,094 the disclosures of all of the above being incorporated herein by reference in their entirety.

FIELD OF THE INVENTION

This invention relates to compositions comprising a high molecular weight, water soluble polymer having a cloud point from about 20 to about 90° C., and one or more carrageenans. The compositions may be conveniently molded into components of pharmaceutical dosage forms, e.g. a shell over a core comprising active ingredient, and as such provide burst release of the active ingredient from the dosage form.

BACKGROUND OF THE INVENTION

A variety of cellulosic polymers are known to be useful in the preparation of dosage forms. They are often combined with other polymers and used as coatings or shells for dosage forms. For example, WO 01/32150 discloses an edible, hardenable coating composition containing microcrystalline cellulose, carrageenan, and at least one of a strengthening polymer, a plasticizer, a surface active agent or a combination thereof. The composition provides a prompt, i.e., immediate, release coating for solid dosage forms and is applied by spray coating.

WO 00/40223 relates to a composition comprising hydroxypropylcellulose and at least one anionic polymer such as carboxymethyl ether salts of cellulose, methacrylic acid polymers and copolymers, carboxyvinyl polymers and copolymers, alginic acid salts, pectinic acid salts, pectic acid salts, carrageenan, agar and carboxylic acid salts of polysaccharides. The ratio of hydroxypropylcellulose to anionic polymer is from 1:20 to 20:1. The composition is used as an aqueous solution to coat substrates.

U.S. Pat. No. 6,358,525 B1 discloses a pharmaceutical composition containing a medicament and a blend of two components. The first component is hydroxypropylcellulose and the second component is at least one other polymer selected from a group that includes carrageenan, agar, and gellan gum. The pharmaceutical composition is formed into a tablet that may be coated with a conventional coating material.

U.S. Pat. No. 6,245,356 B1 relates to a sustained release, oral, solid dosage form comprising agglomerated particles of a therapeutically active medicament in amorphous form, a gelling agent, an ionizable gel strength enhancing agent and an inert diluent. The gelling agent preferably comprises xanthan gum and locust bean gum, but may alternatively comprise alginates, carrageenan, pectin, and other compounds. The ionizable gel strength enhancing agent may be a monovalent or multivalent metal cation. The active medicament in amorphous form, gelling agent, ionizable gel strength enhancing agent and an inert diluent are mixed or granulated together and formed into a tablet.

Known compositions comprising water soluble polymers are often difficult to use, for example in coating operations, because their viscosity becomes too high, especially with increasing polymer concentrations, or increasing polymer molecular weight. Spraying and molding processes can be particularly difficult. Accordingly, dilute solutions must be used, resulting in lengthy processing times to build up adequate thickness.

Applicants have now discovered that a composition comprising a combination of a high molecular weight, water soluble polymer having a cloud point from about 20 to about 90° C. and one or more carrageenans, in certain embodiments with gellan gum and in other embodiments with both gellan gum and a lubricant, may be used as a component of a dosage form, for example as the shell of a dosage form containing active ingredient in an underlying core. The high molecular weight, water soluble polymer and the carrageenan can be dispersed in water, along with other ingredients, at a temperature above the cloud point of the high molecular weight, water soluble polymer, leaving the high molecular weight, water soluble polymer undissolved and the viscosity of the dispersion manageable. The dispersion flows easily, and sets quickly and strongly at a relatively high temperature due to the presence of the carrageenan. Cores containing active ingredient can advantageously be coated with this composition, preferably by molding, to prepare dosage forms that provide a burst release of the active ingredient.

SUMMARY OF THE INVENTION

In one embodiment, the invention provides a composition comprising 40 to 95 weight percent of a high molecular weight, water soluble polymer having a cloud point from about 20 to about 90° C., 5 to 25 weight percent carrageenan, and 0.5 to 5 weight percent gellan gum.

In another embodiment, the invention provides a composition consisting essentially of: a) 40 to 95 weight percent of hydroxypropyl methylcellulose having a viscosity from about 80 to about 120,000 mPa s in 2% aqueous solution; b) 5 to 25 weight percent carrageenan, c) 0.5 to 5 weight percent gellan gum; d) up to 10 weight percent potassium chloride; and e) 5 to 20 weight percent of glyceryl monostearate.

In another embodiment, the invention relates to an aqueous dispersion comprising: a) 8 to 20 weight percent of a high molecular weight, water soluble polymer having a cloud point from about 20 to about 90° C.; b) 1 to 3 weight percent carrageenan; c) 0.2 to 1 weight percent gellan gum; and about 80 weight percent water.

In a further embodiment, the invention provides an aqueous dispersion consisting essentially of: a) 8 to 20 weight percent of hydroxypropyl methylcellulose having a viscosity from about 80 to about 120,000 mPa s in 2% aqueous solution; b) 1 to 3 weight percent carrageenan; c) 0.2 to 1 weight percent gellan gum; d) up to 2 weight percent of potassium chloride; e) 1 to 5 weight percent of glyceryl monostearate; and f) about 80 weight percent water.

In another embodiment, the invention provides a composition comprising 40 to 95 weight percent of a high molecular weight, water soluble polymer having a cloud point from about 20 to about 90° C., 5 to 40 weight percent of one or more carrageenans, and 0.5 to 30 weight percent lubricant.

In a further embodiment, the invention provides a composition consisting essentially of: a) 40 to 95 weight percent of hydroxypropyl methylcellulose having a viscosity from about 80 to about 120,000 mPa s in 2% aqueous solution; b) 5 to 40 weight percent of one or more carrageenans, c) up to 10 weight percent potassium chloride; and d) 5 to 40 weight percent of glyceryl monostearate.

The invention also provides an aqueous dispersion comprising: a) 8 to 20 weight percent of a high molecular weight, water soluble polymer having a cloud point from about 20 to about 90° C.; b) 1 to 5 weight percent of one or more carrageenans; c) 0.1 to 6 weight percent glyceryl monostearate; and d) about 80 weight percent water.

The invention further provides an aqueous dispersion consisting essentially of: a) 8 to 20 weight percent of hydroxypropyl methylcellulose having a viscosity from about 80 to about 120,000 mPa s in 2% aqueous solution; b) 1 to 5 weight percent of one or more carrageenans; c) up to 2 weight percent of potassium chloride; d) 0.1 to 6 weight percent of glyceryl monostearate; and e) about 80 weight percent water.

DETAILED DESCRIPTION OF THE INVENTION

Figure 1:
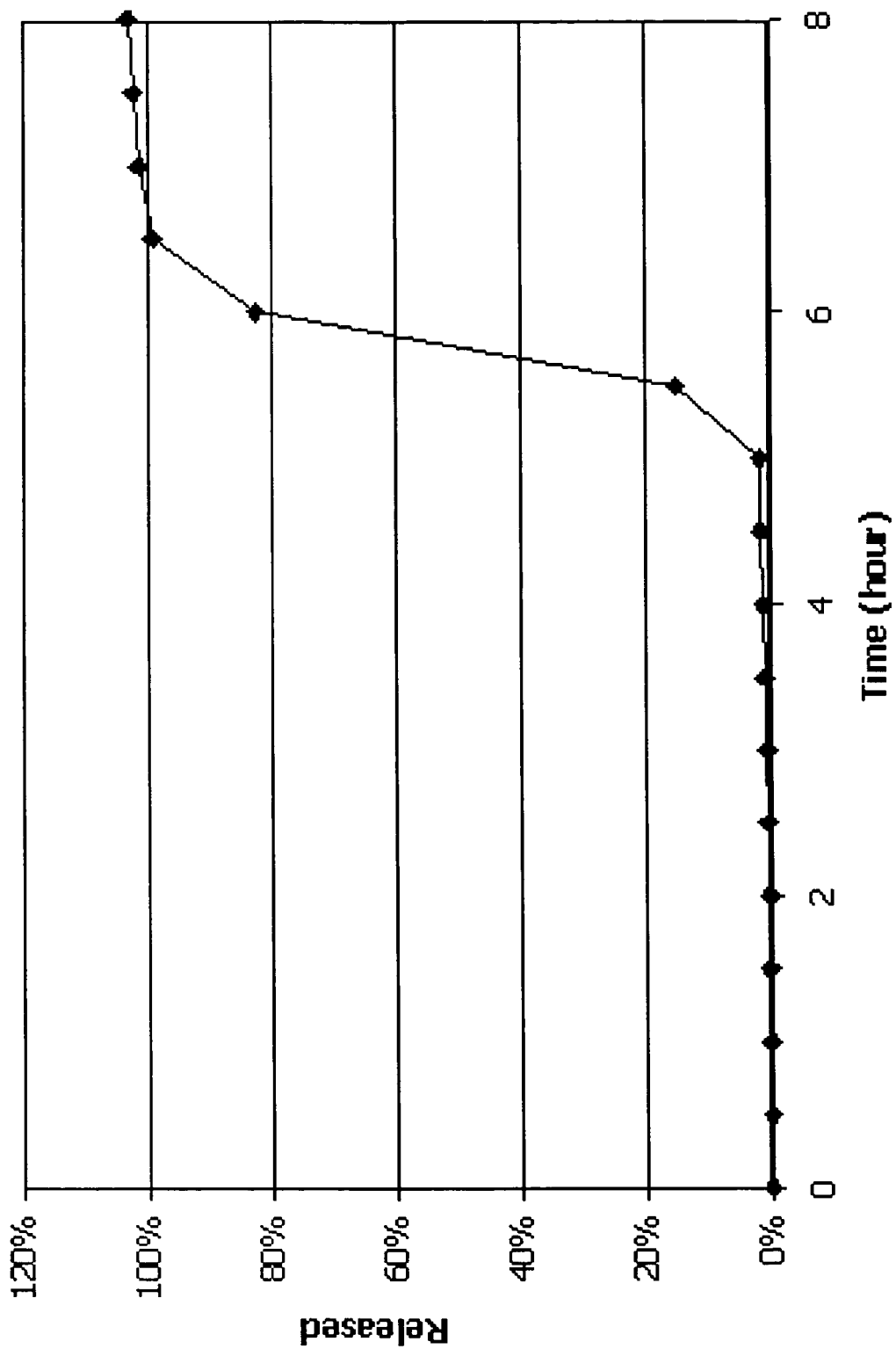
FIGS. 1 and 2 depict the percent release of active ingredient versus hours for the dosage forms of Example 1 and Example 2, respectively.

As used herein, the term "dosage form" applies to any solid object, semi-solid, or liquid composition designed to contain a specific pre-determined amount (dose) of a certain ingredient, for example an active ingredient as defined below. Suitable dosage forms may be pharmaceutical drug delivery systems, including those for oral administration, buccal administration, rectal administration, topical or mucosal delivery, or subcutaneous implants, or other implanted drug delivery systems; or compositions for delivering minerals, vitamins and other nutraceuticals, oral care agents, flavorants, and the like. Preferably the dosage forms of the present invention are considered to be solid, however they may contain liquid or semi-solid components. In a particularly preferred embodiment, the dosage form is an orally administered system for delivering a pharmaceutical active ingredient to the gastro-intestinal tract of a human.

Suitable active ingredients for use in this invention include for example pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable oral care agents include breath fresheners, tooth whiteners, antimicrobial agents, tooth mineralizers, tooth decay inhibitors, topical anesthetics, mucoprotectants, and the like.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment of the invention, the active ingredient may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active ingredient is selected from analgesics, anti-inflammatories, and antipyretics, e.g. non-steroidal anti-inflammatory drugs (NSAIDs), including propionic acid derivatives, e.g. ibuprofen, naproxen, ketoprofen and the like; acetic acid derivatives, e.g. indomethacin, diclofenac, sulindac, tolmetin, and the like; fenamic acid derivatives, e.g. mefanamic acid, meclofenamic acid, flufenamic acid, and the like; biphenylcarbodylic acid derivatives, e.g. diflunisal, flufenisal, and the like; and oxicams, e.g. piroxicam, sudoxicam, isoxicam, meloxicam, and the like. In one particular embodiment, the active ingredient is selected from propionic acid derivative NSAID, e.g. ibuprofen, naproxen, flurbiprofen, fenbufen, fenoprofen, indoprofen, ketoprofen, fluprofen, pirprofen, carprofen, oxaprozin, pranoprofen, suprofen, and pharmaceutically acceptable salts, derivatives, and combinations thereof. In another particular embodiment of the invention, the active ingredient may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment of the invention, the active ingredient may be selected from pseudoephedrine, phenylpropanolamine, chlorpheniramine, dextromethorphan, diphenhydramine, astemizole, terfenadine, fexofenadine, loratadine, desloratadine, cetirizine, mixtures thereof and pharmaceutically acceptable salts, esters, isomers, and mixtures thereof.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors must be considered, as known in the art. Typically, the dosage form comprises at least about 1 weight percent, preferably, the dosage form comprises at least about 5 weight percent, e.g. at least about 25 weight percent of a combination of one or more active ingredients. In one embodiment, a core comprises a total of at least about 50 weight percent, e.g. at least about 70 weight percent, say at least about 80 weight percent (based on the weight of the core) of one or more active ingredients.

The active ingredient or ingredients may be present in the dosage form in any form. For example, the active ingredient may be dispersed at the molecular level, e.g. melted or dissolved, within the dosage form, or may be in the form of particles, which in turn may be coated or uncoated. If the active ingredient is in form of particles, the particles (whether coated or uncoated) typically have an average particle size of about 1-2000 microns. In one embodiment, such particles are crystals having an average particle size of about 1-300 microns. In another embodiment, the particles are granules or pellets having an average particle size of about 50-2000 microns, for example about 50-1000 microns, say about 100-800 microns.

The composition of the invention comprises a combination of a high molecular weight, water soluble polymer, one or more carrageenans, and gellan gum and/or a lubricant such as glyceryl monostearate. It is a solid and is preferably substantially free of pores having a diameter of 0.5 to 5.0 microns. It may be used as a component of a pharmaceutical dosage form, such as the shell of a dosage form, a portion of a shell of a dosage form, the core of a dosage form, a portion of the core of a dosage form, or combined with one or more active ingredients into a dosage form per se in which case it may optionally be coated with conventional coating materials, as well known in the art.

The high molecular weight, water soluble polymer has a cloud point from about 20 to about 90° C. Preferably, the high molecular weight, water soluble polymer has a cloud point from about 35 to about 70° C. The weight average molecular weight of the high molecular weight, water soluble polymer may be in the range of about 1000 to about 2,000,000 g/mole.

Examples of suitable high molecular weight, water soluble polymers include hydroxypropylmethyl cellulose, hydroxypropyl cellulose, methyl cellulose, polyvinyl alcohol, and mixtures thereof.

In one embodiment, the high molecular weight, water soluble polymer comprises hydroxypropyl cellulose having a weight average molecular weight from about 140,000 to about 1,150,000. In another embodiment, the high molecular weight, water soluble polymer comprises hydroxypropyl methylcellulose having a viscosity from about 80 to about 120,000 mPa s in 2% aqueous solution. In a further embodiment, the high molecular weight, water soluble polymer comprises methylcellulose having a viscosity of 4000 mPa s in 2% aqueous solution. In yet another embodiment, the high molecular weight, water soluble polymer comprises polyvinyl alcohol having a weight average molecular weight from about 30,000 to about 200,000.

The composition also comprises one or more carrageenans. The carrageenan is typically present in an amount from about 5 to about 40, or 5 to about 25 weight percent of the composition. Examples of carrageenans include Kappa, Lambda and Iota carrageenans and combinations thereof. In one embodiment, the carrageenan comprises a Kappa carrageenan. In another embodiment, the carrageenan comprises a combination of Kappa and Lambda carrageenans.

In one embodiment, the composition further comprises gellan gum, preferably in the range of about 0.5 to about 5 weight percent of the composition. Examples of useful gellan gums include unclarified low acyl, clarified low acyl, and unclarified high acyl gellan gum and combinations thereof. In one embodiment, the gellan gum comprises unclarified high acyl gellan gum Accordingly, the composition in one embodiment comprises about 40 to about 95 weight percent of a high molecular weight, water soluble polymer having a cloud point from about 20 to about 90° C., 5 to 25 weight percent carrageenan, and 0.5 to 5 weight percent gellan gum.

In another embodiment, the composition consists essentially of a) 40 to 95 weight percent of hydroxypropyl methylcellulose having a viscosity from about 80 to about 120,000 mPa s in 2% aqueous solution; b) 5 to 25 weight percent carrageenan, c) 0.5 to 5 weight percent gellan gum; d) up to 10 weight percent potassium chloride; and e) 5 to 20 weight percent of glyceryl monostearate.

In another embodiment, the composition further comprises a lubricant, preferably in the range of about 0.5 to about 30 weight percent of the composition. The lubricant may be, for example, glyceryl monostearate, glyceryl palmitostearate, glycerol monooleate, hydrogenated vegetable oil, type I, magnesium stearate, and talc. Preferably, the lubricant is glyceryl monostearate.

Accordingly, the composition in one embodiment comprises 40 to 95 weight percent of a high molecular weight, water soluble polymer having a cloud point from about 20 to about 90° C., 5 to 40 weight percent of one or more carrageenans, and 0.5 to 30 weight percent lubricant.

In another embodiment, the composition consists essentially of: a) 40 to 95 weight percent of hydroxypropyl methylcellulose having a viscosity from about 80 to about 120,000 mPa s in 2% aqueous solution; b) 5 to 40 weight percent of one or more carrageenans, c) up to 10 weight percent potassium chloride; and d) 5 to 40 weight percent of glyceryl monostearate.

In another embodiment, the composition also comprises active ingredient. When active ingredient is present, the level of high molecular weight water soluble polymer in the composition is adjusted downward by the amount of the active ingredient. In one particular embodiment, the composition comprises up to about 80 weight percent of at least one active ingredient; about 15 to about 95 weight percent of a high molecular weight, water soluble polymer having a cloud point from about 20 to about 90° C.; and about 5 to about 25 weight percent carrageenans.

The composition, whether used as a shell, portion of a shell, i.e. "shell portion," core, core portion, or as a dosage form per se, may comprise other optional ingredients. In one embodiment, the composition also comprises an inorganic cation. Suitable inorganic cations include pharmaceutically acceptable monovalent, divalent, and trivalent cations. For example, the inorganic cation may be selected from the group consisting of potassium cations, calcium cations, and mixtures thereof.

In another embodiment, the composition also comprises a water-insoluble polymer. Suitable water-insoluble polymers include of ethyl cellulose, cellulose acetate, cellulose acetate butyrate and mixtures thereof.

In one embodiment, a dosage form according to the invention comprises a core at least partially surrounded by a shell or a shell portion that comprises a high molecular weight, water soluble polymer, carrageenan, and gellan gum and/or a lubricant. Such shell may comprise about 1 to about 75, or about 2 to about 24, or about 5 to about 15, weight percent of the total weight of the dosage form. The average thickness of the shell or shell portion may be in the range of about 50 to about 500 microns.

The shell may completely surround the core, or only partially surround the core. Moreover, only one shell portion may comprise the composition of the invention, as further discussed below. For example, in one embodiment a shell comprising a first shell portion and a second shell portion surrounds the core, and the first shell portion comprises the composition of the present invention, while the second shell portion is compositionally different from the first shell portion. In embodiments wherein a first shell portion of a dosage form comprises the composition of the present invention, the weight of said first shell portion may be from about 1 to about 75, e.g. about 1 to about 25, or about 1 to about 10 percent of the weight of the dosage form.

In embodiments in which the composition is employed as a first shell portion, the second shell portion may comprise any suitable materials, and be applied by any suitable method, for example, those disclosed in U.S. application Ser. Nos. 10/432,488 filed Sep. 28, 2002; 10/432,504, filed Sep. 28, 2002; 10/432,812, filed Sep. 28, 2002; and 10/393,610, filed Mar. 21, 2003, the disclosures of which are incorporated herein by reference.

The core may be any solid form. The core may prepared by any suitable method, including for example compression or molding. As used herein, "core" refers to a material which is at least partially enveloped or surrounded by another material. Preferably, the core is a self-contained unitary object, such as a tablet or capsule. Typically, the core comprises a solid, for example, the core may be a compressed or molded tablet, hard or soft capsule, suppository, or a confectionery form such as a lozenge, nougat, caramel, fondant, or fat based composition. In certain other embodiments, the core or a portion thereof may be in the form of a semi-solid or a liquid in the finished dosage form. For example the core may comprise a liquid filled capsule, or a semisolid fondant material. In embodiments in which the core comprises a flowable component, such as a plurality of granules or particles, or a liquid, the core preferably additionally comprises an enveloping component, such as a capsule shell, or a coating, for containing the flowable material. In certain particular embodiments in which the core comprises an enveloping component, the shell or shell portions of the present invention are in direct contact with the enveloping component of the core, which separates the shell from the flowable component of the core.

In one embodiment the core is a compressed tablet having a hardness from about 2 to about 30 kp/cm$^2$, e.g. from about 6 to about 25 kp/cm$^2$. "Hardness" is a term used in the art to describe the diametral breaking strength of either the core or the coated solid dosage form as measured by conventional pharmaceutical hardness testing equipment, such as a Schleuniger Hardness Tester. In order to compare values across different size tablets, the breaking strength must be normalized for the area of the break. This normalized value, expressed in kp/cm$^2$, is sometimes referred in the art as tablet tensile strength. A general discussion of tablet hardness testing is found in Leiberman et al., *Pharmaceutical Dosage Forms—Tablets*, Volume 2, 2$^{nd}$ ed., Marcel Dekker Inc., 1990, pp. 213-217, 327-329.

The core may have one of a variety of different shapes. For example, the core may be shaped as a polyhedron, such as a cube, pyramid, prism, or the like; or may have the geometry of a space figure with some non-flat faces, such as a cone, truncated cone, cylinder, sphere, torus, or the like. In certain embodiments, a core has one or more major faces. For example, in embodiments wherein a core is a compressed tablet, the core surface typically has two opposing major faces formed by contact with the upper and lower punch faces in the compression machine. In such embodiments the core surface typically further comprises a "belly-band" located between the two major faces, and formed by contact with the die walls in the compression machine. A core may also comprise a multilayer tablet. Exemplary core shapes that may be employed include tablet shapes formed from compression tooling shapes described by "The Elizabeth Companies Tablet Design Training Manual" (Elizabeth Carbide Die Co., Inc., p. 7 (McKeesport, Pa.) (incorporated herein by reference).

The core typically comprises active ingredient and a variety of excipients, depending on the method by which it is made.

In embodiments in which the core is made by compression, suitable excipients include fillers, binders, disintegrants, lubricants, glidants, and the like, as known in the art. A core made by compression may be a single or multi-layer, for example bi-layer, tablet.

Suitable fillers for use in making the core by compression include water-soluble compressible carbohydrates such as sugars, which include dextrose, sucrose, maltose, and lactose, sugar-alcohols, which include mannitol, sorbitol, maltitol, xylitol, starch hydrolysates, which include dextrins, and maltodextrins, and the like, water insoluble plastically deforming materials such as microcrystalline cellulose or other cellulosic derivatives, water-insoluble brittle fracture materials such as dicalcium phosphate, tricalcium phosphate and the like and mixtures thereof.

Suitable binders for making the core by compression include dry binders such as polyvinyl pyrrolidone, hydroxypropylmethylcellulose, and the like; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, starches, and the like; and derivatives and mixtures thereof.

Suitable disintegrants for making the core by compression, include sodium starch glycolate, cross-linked polyvinylpyrrolidone, cross-linked carboxymethylcellulose, starches, microcrystalline cellulose, and the like.

Suitable lubricants for making the core by compression include long chain fatty acids and their salts, such as magnesium stearate and stearic acid, talc, glycerides and waxes.

Suitable glidants for making the core by compression include colloidal silicon dioxide, and the like.

In certain embodiments, the core or a portion thereof may optionally comprise release modifying excipients as known in the art, for example as disclosed in commonly assigned, copending U.S. application Ser. No. 10/432,488, the disclosure of which is incorporated by reference herein. Suitable release-modifying excipients for making the core by compression include swellable erodible hydrophillic materials, insoluble edible materials, pH-dependent polymers, and the like.

Suitable pharmaceutically acceptable adjuvants for making the cores by compression include, preservatives; high intensity sweeteners such as aspartame, acesulfame potassium, sucralose, and saccharin; flavorants; colorants; antioxidants; surfactants; wetting agents; and the like and mixtures thereof.

In embodiments wherein the core is prepared by compression, a dry blending (i.e. direct compression), or wet granulation process may be employed, as known in the art. In a dry blending (direct compression) method, the active ingredient or ingredients, together with the excipients, are blended in a suitable blender, then transferred directly to a compression machine for pressing into tablets. In a wet granulation method, the active ingredient or ingredients, appropriate excipients, and a solution or dispersion of a wet binder (e.g. an aqueous cooked starch paste, or solution of polyvinyl pyrrolidone) are mixed and granulated. Alternatively a dry binder may be included among the excipients, and the mixture may be granulated with water or other suitable solvent. Suitable apparatuses for wet granulation are known in the art, including low shear, e.g. planetary mixers; high shear mixers; and fluid beds, including rotary fluid beds. The resulting granulated material is dried, and optionally dry-blended with further ingredients, e.g. adjuvants and/or excipients such as for example lubricants, colorants, and the like. The final dry blend is then suitable for compression. Methods for direct compression and wet granulation processes are known in the art, and are described in detail in, for example, Lachman, et al., *The Theory and Practice of Industrial Pharmacy*, Chapter 11 (3rd ed. 1986).

The dry-blended, or wet granulated, powder mixture is typically compacted into tablets using a rotary compression machine as known in the art, such as for example those commercially available from Fette America Inc., Rockaway, N.J., or Manesty Machines LTD, Liverpool, UK. In a rotary compression machine, a metered volume of powder is filled into a die cavity, which rotates as part of a "die table" from the filling position to a compaction position where the powder is compacted between an upper and a lower punch to an ejection position where the resulting tablet is pushed from the die cavity by the lower punch and guided to an ejection chute by a stationary "take-off" bar.

In one optional embodiment, the core may be prepared by the compression methods and apparatus described in copending U.S. patent application Ser. No. 09/966,509, pages 16-27, the disclosure of which is incorporated herein by reference. Specifically, the core is made using a rotary compression module comprising a fill zone, insertion zone, compression zone, ejection zone, and purge zone in a single apparatus having a double row die construction as shown in FIG. 6 of U.S. patent application Ser. No. 09/966,509. The dies of the compression module are preferably filled using the assistance of a vacuum, with filters located in or near each die.

The shell may be substantially unitary and continuous, or the shell may comprise multiple portions, e.g. a first shell portion and a second shell portion. In certain embodiments, at least one such shell portion comprises the composition of the invention. In certain embodiments the shell or shell portions are in direct contact with the core. In certain other embodiments, the shell or shell portions are in direct contact with a subcoating that substantially surrounds the core. In certain embodiments, the shell or a shell portion may comprise one ore more openings therein.

In embodiments in which the shell or shell portion is applied to the core by molding, at least a portion of the shell surrounds the core such that the shell inner surface resides substantially conformally upon the core outer surface. As used herein, the term "substantially conformally" shall mean that the inner surface of the shell has peaks and valleys or indentations and protrusions corresponding substantially inversely to the peaks and valleys of the outer surface of the core. In certain such embodiments, the indentations and protrusions typically have a length, width, height or depth in one dimension of greater than 10 microns, say greater than 20 microns, and less than about 30,000 microns, preferably less than about 2000 microns.

In certain embodiments, the shell comprises a first shell portion and a second shell portion that are compositionally different. In one embodiment, a first shell portion comprises the composition of the invention, and a second shell portion is compositionally different from the first shell portion. As used herein, the term "compositionally different" means having features that are readily distinguishable by qualitative or quantitative chemical analysis, physical testing, or visual observation. For example, the first and second shell portions may contain different ingredients, or different levels of the same ingredients, or the first and second shell portions may have different physical or chemical properties, different functional properties, or be visually distinct. Examples of physical or chemical properties that may be different include hydrophylicity, hydrophobicity, hygroscopicity, elasticity, plasticity, tensile strength, crystallinity, and density. Examples of functional properties which may be different include rate and/or extent of dissolution of the material itself or of an active ingredient therefrom, rate of disintegration of the material, permeability to active ingredients, permeability to water or aqueous media, and the like. Examples of visual distinctions include size, shape, topography, or other geometric features, color, hue, opacity, and gloss.

In one embodiment, the dosage form of the invention comprises: a) a core containing an active ingredient; b) an optional subcoating that substantially covers the core; and c) a shell comprising first and second shell portions residing on the surface of the subcoating, the first shell portion comprising the composition of the invention. As used herein, "substantially covers" shall mean at least about 95 percent of the surface area of the core is covered by the subcoating.

The use of subcoatings is well known in the art and disclosed in, for example, U.S. Pat. No. 3,185,626, which is incorporated by reference herein. Any composition suitable for film-coating a tablet may be used as a subcoating according to the present invention. Examples of suitable subcoatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Additional suitable subcoatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates, pigments, and opacifiers.

In one embodiment, the subcoating comprises from about 2 percent to about 8 percent, e.g. from about 4 percent to about 6 percent of a water-soluble cellulose ether and from about 0.1 percent to about 1 percent, castor oil, as disclosed in detail in U.S. Pat. No. 5,658,589, which is incorporated by reference herein. In another embodiment, the subcoating comprises from about 20 percent to about 50 percent, e.g., from about 25 percent to about 40 percent of HPMC; from about 45 percent to about 75 percent, e.g., from about 50 percent to about 70 percent of maltodextrin; and from about 1 percent to about 10 percent, e.g., from about 5 percent to about 10 percent of PEG 400.

The dried subcoating typically is present in an amount, based upon the dry weight of the core, from about 0 percent to about 5 percent.

In one embodiment, an aqueous dispersion of the composition comprising the high molecular weight, water soluble polymer and carrageenan, along with gellan gum and/or a lubricant, is used to prepare the shell. In particular, these ingredients are dispersed in water at a temperature above the cloud point of the high molecular weight, water soluble polymer. The dispersion is applied to a core, by for example molding, dipping, spraying, or other means. Preferably, the dispersion is applied to the core by molding. Spraying is least preferred. After application of the dispersion to the core, the core is cooled, preferably at a relatively high temperature, i.e., above the cloud point of the high molecular weight, water soluble polymer.

The aqueous dispersion typically comprises about 5 to about 40 weight percent solids. In one embodiment, the aqueous dispersion comprises about 10 to about 30 weight percent solids.

In one embodiment, the high molecular weight, water soluble polymer comprises about 8 to about 20 weight percent of the total weight of the aqueous dispersion.

In another embodiment, the aqueous dispersion comprises about 0 0.5 to about 6 weight percent carrageenan and 0.2 to about 3 weight percent gellan gum.

In a further embodiment, the aqueous dispersion comprises about 0.5 to about 7 weight percent carrageenan and 0.1 to about 6 weight percent lubricant such as glyceryl monostearate.

The shell thickness at various locations may be measured using a microscope, for example, an environmental scanning electron microscope, model XL 30 ESEM LaB6, Philips Electronic Instruments Company, Mahwah, Wis. The shell thickness is measured at 6 different locations on a single dosage form. The relative standard deviation (RSD) is calculated as the sample standard deviation, devided by the mean, times 100 as known in the art (i.e. the RSD is the standard deviation expressed as a percentage of the mean). The RSD in shell thickness provides an indication of the variation in the thickness of the shell on a single dosage form. In certain optional embodiments of the invention, the relative standard deviation in shell thickness is less than about 40%, e.g less than about 30%, or less than about 20%.

The shell itself or an outer coating thereon may optionally contain active ingredient. In one embodiment, such active ingredient will be released immediately from the dosage form upon ingestion, or contacting of the dosage form with a liquid medium. In another embodiment, such active ingredient will be released in a controlled, sustained, prolonged, or extended fashion upon ingestion, or contacting of the dosage form with a liquid medium.

In certain embodiments of the invention, the core, the shell, or the composition is prepared by molding. In such embodiments, the core, the shell, or the composition is made from a dispersion as described above optionally comprising active ingredient. The dispersion comprises the high molecular weight, water soluble polymer dispersed in a liquid carrier comprising the carrageenan along with the gellan gum and/or lubricant and a liquid plasticizer at a temperature above the cloud point of the high molecular weight polymer and above the gelling temperature of the carrageenan and gellan gum. Suitable liquid plasticizers include water, glycerin, propylene glycol, triacetin, triethyl citrate, polyethylene glycol, sorbitol, tribuyl citrate, and mixtures thereof.

In one embodiment, molding is performed via thermal setting molding using the method and apparatus described in copending U.S. patent application Ser. No. 09/966,450, pages 57-63, the disclosure of which is incorporated herein by reference. In this embodiment, the composition is formed by injecting the dispersion into a molding chamber. The dispersion is cooled and solidifies in the molding chamber into a shaped form (i.e., having the shape of the mold).

According to this method, the dispersion may comprise solid particles of the high molecular weight, water-soluble polymer suspended in a liquid carrier comprising the other ingredients (carrageenan, gellan gum and/or lubricant) and the liquid plasticizer, e.g. water. Here, the other ingredients are dissolved in the liquid plasticizer.

In another embodiment, molding is performed by thermal cycle molding using the method and apparatus described in copending U.S. patent application Ser. No. 09/966,497, pages 27-51, the disclosure of which is incorporated herein by reference. Thermal cycle molding is performed by injecting the dispersion into a heated molding chamber. In this embodiment, the dispersion may comprise the high molecular weight water soluble polymer dispersed in a liquid carrier comprising carrageenan along with gellan gum and/or lubricant and water at a temperature above the cloud point of the high molecular weight polymer and above the gelling temperature of the other polymers. The dispersion is cooled and solidifies in the molding chamber into a shaped form (i.e., having the shape of the mold).

In the thermal cycle molding method and apparatus of U.S. patent application Ser. No. 09/966,497 a thermal cycle molding module having the general configuration shown in FIG. 3 therein is employed. The thermal cycle molding module 200 comprises a rotor 202 around which a plurality of mold units 204 are disposed. The thermal cycle molding module includes a reservoir 206 (see FIG. 4) for holding dispersion. In addition, the thermal cycle molding module is provided with a temperature control system for rapidly heating and cooling the mold units. FIGS. 55 and 56 depict the temperature control system 600.

The mold units may comprise center mold assemblies 212, upper mold assemblies 214, and lower mold assemblies 210, as shown in FIGS. 26-28, which mate to form mold cavities having a desired shape, for instance of a core or a shell surrounding one or more cores. As rotor 202 rotates, opposing center and upper mold assemblies or opposing center and lower mold assemblies close. Dispersion, which is heated to a flowable state in reservoir 206, is injected into the resulting mold cavities. The temperature of the dispersion is then decreased, hardening the dispersion. The mold assemblies open and eject the finished product.

In one optional embodiment of the invention, the shell is applied to the dosage form using a thermal cycle molding apparatus of the general type shown in FIGS. 28A-C of copending U.S. application Ser. No. 09/966,497 comprising rotatable center mold assemblies 212, lower mold assemblies 210 and upper mold assemblies 214. Cores are continuously fed to the mold assemblies. Dispersion for making the shell, which is heated to a flowable state in reservoir 206, is injected into the mold cavities created by the closed mold assemblies holding the cores. The temperature of the shell dispersion is then decreased, hardening it around the cores. The mold assemblies open and eject the finished dosage forms. Shell coating is performed in two steps, each half of the dosage forms being coated separately as shown in the flow diagram of FIG. 28B of copending U.S. application Ser. No. 09/966,939 via rotation of the center mold assembly.

In one embodiment, the compression module of copending U.S. patent application Ser. No. 09/966,509, pp. 16-27 may be employed to make the core and the shell is applied to the core using a thermal cycle molding module as described above. A transfer device as described in U.S. patent application Ser. No. 09/966,414, pp. 51-57, the disclosure of which is incorporated herein by reference, may be used to transfer the cores from the compression module to the thermal cycle molding module. Such a transfer device may have the structure shown as 300 in FIG. 3 of copending U.S. application Ser. No. 09/966,939. It comprises a plurality of transfer units 304 attached in cantilever fashion to a belt 312 as shown in FIGS. 68 and 69 of copending U.S. application Ser. No. 09/966,939. The transfer device rotates and operates in sync with the compression module and the thermal cycle molding module to which it is coupled. Transfer units 304 comprise retainers 330 for holding cores as they travel around the transfer device.

In certain embodiments wherein a liquid carrier for the dispersion is formed from a mixture of carrageenan with gellan gum and/or lubricant and a liquid plasticizer, the liquid carrier may be a thermoplastic system. For example when the carrageenan and gellan gum are melted and mixed with the liquid plasticizer in a certain ratio, the mixture can be in a thermoplastic state depending on temperature and pressure. In certain other embodiments, the liquid carrier is not a thermoplastic system.

In certain optional embodiments the shell, core, or the composition of the invention may additionally comprise a water insoluble polymer at a level of up to about 40%, e.g 15% of the weight of the shell, core, or the composition of the invention. In embodiments wherein a water insoluble polymer is employed, the weight ratio of high molecular weight water soluble polymer to water insoluble polymer may be from about 99:1 to about 50:50. Suitable water insoluble polymers include ethyl cellulose, cellulose acetate, cellulose acetate butyrate, cellulose propionate, and mixtures thereof.

The dispersion for making cores or the shell by molding may optionally comprise adjuvants or excipients, which may comprise up to about 30% by weight of the dispersion. Examples of suitable adjuvants or excipients include detackifiers, humectants, surfactants, anti-foaming agents, colorants, flavorants, sweeteners, opacifiers, and the like.

In embodiments in which the composition is prepared by molding, the composition typically is preferably substantially free of pores in the diameter range of 0.5 to 5.0 microns, i.e. has a pore volume in the pore diameter range of 0.5 to 5.0 microns of less than about 0.02 cc/g, preferably less than about 0.01 cc/g, more preferably less than about 0.005 cc/g. Typical compressed materials have pore volumes in this diameter range of more than about 0.02 cc/g. Pore volume, pore diameter and density may be determined using a Quantachrome Instruments PoreMaster 60 mercury intrusion porosimeter and associated computer software program known as "Porowin." The procedure is documented in the Quantachrome Instruments PoreMaster Operation Manual. The PoreMaster determines both pore volume and pore diameter of a solid or powder by forced intrusion of a non-wetting liquid (mercury), which involves evacuation of the sample in a sample cell (penetrometer), filling the cell with mercury to surround the sample with mercury, applying pressure to the sample cell by: (i) compressed air (up to 50 psi maximum); and (ii) a hydraulic (oil) pressure generator (up to 60000 psi maximum). Intruded volume is measured by a change in the capacitance as mercury moves from outside the sample into its pores under applied pressure. The corresponding pore size diameter (d) at which the intrusion takes place is calculated directly from the so-called "Washburn Equation": $d=-(4\gamma (\cos\theta)/P)$ where $\gamma$ is the surface tension of liquid mercury, $\theta$ is the contact angle between mercury and the sample surface and P is the applied pressure.

Equipment used for pore volume measurements:
1. Quantachrome Instruments PoreMaster 60.
2. Analytical Balance capable of weighing to 0.0001 g.
3. Desiccator.

Reagents used for measurements:
1. High purity nitrogen.
2. Triply distilled mercury.
3. High pressure fluid (Dila AX, available from Shell Chemical Co.).
4. Liquid nitrogen (for Hg vapor cold trap).
5. Isopropanol or methanol for cleaning sample cells.
6. Liquid detergent for cell cleaning.

Procedure:

The samples remain in sealed packages or as received in the dessicator until analysis. The vacuum pump is switched on, the mercury vapor cold trap is filled with liquid nitrogen, the compressed gas supply is regulated at 55 psi., and the instrument is turned on and allowed a warm up time of at least 30 minutes. The empty penetrometer cell is assembled as described in the instrument manual and its weight is recorded. The cell is installed in the low pressure station and "evacuation and fill only" is selected from the analysis menu, and the following settings are employed:

Fine Evacuation time: 1 min.
Fine Evacuation rate: 10
Coarse Evacuation time: 5 min.

The cell (filled with mercury) is then removed and weighed. The cell is then emptied into the mercury reservoir, and two tablets from each sample are placed in the cell and the cell is reassembled. The weight of the cell and sample are then recorded. The cell is then installed in the low-pressure station, the low-pressure option is selected from the menu, and the following parameters are set:

Mode: Low pressure
Fine evacuation rate: 10
Fine evacuation until: 200 µHg
Coarse evacuation time: 10 min.
Fill pressure: Contact+0.1
Maximum pressure: 50
Direction: Intrusion And Extrusion
Repeat: 0
Mercury contact angle: 140
Mercury surface tension: 480

Data acquisition is then begun. The pressure vs. cumulative volume-intruded plot is displayed on the screen. After low-pressure analysis is complete, the cell is removed from the low-pressure station and reweighed. The space above the mercury is filled with hydraulic oil, and the cell is assembled and installed in the high-pressure cavity. The following settings are used:

Mode: Fixed rate
Motor speed: 5
Start pressure: 20
End pressure: 60,000
Direction: Intrusion and extrusion
Repeat: 0
Oil fill length: 5
Mercury contact angle: 140
Mercury surface tension: 480

Data acquisition is then begun and graphic plot pressure vs. intruded volume is displayed on the screen. After the high pressure run is complete, the low- and high-pressure data files of the same sample are merged.

Dosage forms according to the invention preferably provide modified release of at least one active ingredient contained therein. As used herein, the term "modified release" means the release of an active ingredient from a dosage form or a portion thereof in other than an immediate release fashion, i.e., other than immediately upon contact of the dosage form or portion thereof with a liquid medium. As known in the art, types of modified release include delayed or controlled. Types of controlled release include prolonged, sustained, extended, retarded, and the like. Modified release profiles that incorporate a delayed release feature include pulsatile, repeat action, and the like. As is also known in the art, suitable mechanisms for achieving modified release of an active ingredient include diffusion, erosion, surface area control via geometry and/or impermeable barriers, and other known mechanisms known.

In one preferred embodiment, the composition of the invention is used as a shell over a core and provides for delayed burst release of at least one active ingredient contained in the underlying core. That is, release of the active ingredient from the dosage form is delayed for a pre-determined time after ingestion by the patient, after which it is promptly released.

The following non-limiting example further illustrates the invention.

EXAMPLE 1

A dosage form according to the invention was made by coating a core (tablet) prepared as set forth in Part A below with Dispersion A as follows.

A. Preparation of an immediate release ibuprofen core, 404 mg

| Ingredient | Trade Name | Manufacturer | Mg/Tablet |
|---|---|---|---|
| Ibuprofen granules (115 microns) | | Albemarle Corp. Orangeburg, SC | 404.2 |
| Croscarmellose sodium | Ac-Di-Sol | FMC Corp. Philadelphia, PA | 23.7 |
| Magnesium stearate | | Mallinckrodt Speciality Chemicals Co; St. Louis, MO | 2.1 |
| Total | | | 430 |

Prescreened (through a 30 mesh screen) ibuprofen and croscarmellose sodium were mixed in a 1 qt. P-K blender for 5 minutes. Magnesium stearate was added to the mixture and mixed for another 5 minutes. A Beta press (Manesty, Liverpool, UK) equipped with round punch and die unit 0.375" in diameter was used to make the core from the ibuprofen final blend. The compressed core weighed 430 mg and contained 404 mg of ibuprofen.

B. Preparation of Dispersion A

The following ingredients were used to make Dispersion A:

| Ingredient | Trade Name | Manufacturer | Weight (g) | Mg/Tablet |
|---|---|---|---|---|
| Gellan gum | Kelcogel LT100 ® | Kelco Biopolymers, Chicago, IL | 0.53 | 2.3 |
| Carrageenan | Gelcarin GP-812 ® | FMC Corp. Newark, DE | 2.43 | 10.7 |
| Hydroxypropyl methyl cellulose | Methocel K100M Perm CR | The Dow Chemical Co. Midland, MI | 12.74 | 55.8 |
| D.I. Water | | | 84.3 | |

First, a beaker was submersed in an 85° C. water bath (Ret digi-visc; Antal-Direct, Wayne, Pa.). D.I. water was added to the beaker, followed by gellan gum, and the two were mixed with an electric mixer equipped with a propeller style blade until all powder was dispersed. An agitating speed of 1000 rpm was used. The carrageenan powder was added next and then mixed for 15 minutes. The hydroxypropyl methylcellulose powder was added and then mixed for 120 minutes to form Dispersion A in flowable form.

C. Application of Dispersion A to the Cores

A laboratory scale thermal cycle molding unit was used to apply first and second shell portions made from Dispersion A to the core, and comprised a single mold assembly made from an upper mold assembly portion comprising an upper mold cavity, and a lower mold assembly portion comprising a lower mold cavity. The lower mold assembly portion was first cycled to a hot stage at 85° C. for 30 seconds. Dispersion A was introduced into the lower mold cavity. The core from Part A was then inserted into a blank upper mold assembly. The blank upper mold assembly portion was mated with the lower mold assembly portion. The mold assembly was then cycled to a cold stage at 5° C. for 60 seconds to harden the first shell portion. The blank mold assembly portion was removed from the lower mold assembly portion. The upper mold assembly portion was cycled to a hot stage at 85° C. for 30 seconds. A further portion of Dispersion A was added to the upper mold cavity. The lower mold assembly portion, which had been maintained at 5° C., was then mated with the upper mold assembly portion. Both the upper and lower mold assembly portions were cycled to a cold stage at 5° C. for 90 seconds to harden the second shell portion. The lower mold assembly portion was then removed and the finished dosage form, a molded coated core with two halves of the same shell material, was ejected from the upper mold cavity. The finished dosage form was dried at ambient room temperature for 12 hours to remove all residual water. The weight gain due to application of the shell (i.e. the difference in weight between the finished dosage form, and the core) was recorded.

EXAMPLE 2

A core (tablet) prepared as set forth in Example 1, Part A was coated with Dispersion B to prepare a dosage form according to the invention as follows.

A. Preparation of Dispersion B

The following ingredients were used to make Dispersion B:

| Ingredient | Trade Name | Manufacturer | Weight (g) | Mg/Tablet |
|---|---|---|---|---|
| Carrageenan | Viscarin GP-109 ® | FMC Corp. Newark, DE | 1.5 | 7.1 |
| Carrageenan | Gelcarin GP-812 ® | FMC Corp. Newark, DE | 3 | 14.2 |
| Hydroxypropyl methyl cellulose | Methocel K4M Perm CR | The Dow Chemical Co. Midland, MI | 13 | 61.5 |
| Glyceryl monostearate | Myvaplex 600P | Quest International, Hoffman Estates, IL | 2.5 | 11.8 |
| D.I. Water | | | 80 | |

Glyceryl monostearate was dispersed in hot D.I. water and mixed with an electric mixer equipped with a propeller style blade to form a glyceryl monostearate dispersion (20% w/w). A beaker was then submersed in an 85° C. water bath (Ret digi-visc; Antal-Direct, Wayne, Pa.). D.I. water was added to the beaker. Carrageenan powder was added to the beaker and was mixed with an electric mixer equipped with a propeller style blade until all powder was melted. An agitating speed of 1000 rpm was used. The hydroxypropyl methylcellulose powder was then added and mixed for 15 minutes. The glyceryl monostearate dispersion was added and then mixed for 120 minutes to form Dispersion B in flowable form.

B. Application of Dispersion B to the cores:

A laboratory scale thermal cycle molding unit was used to apply first and second shell portions to the cores as described in Example 1 using Dispersion B, except that both the upper and lower mold assembly portions were cycled to a hot stage at 85° C. for 20 seconds and then were cycled to a cold stage at 5° C. for 90 seconds to harden the second shell portion. The finished dosage form, a molded coated core with two halves of the same shell material, was then ejected from the upper mold cavity as in Example 1. The finished dosage form was dried at 50° C. for 12 hours to remove all residual water. The weight gain due to application of the shell (i.e. the difference in weight between the finished dosage form, and the core) was recorded.

EXAMPLE 3

Figure 2:
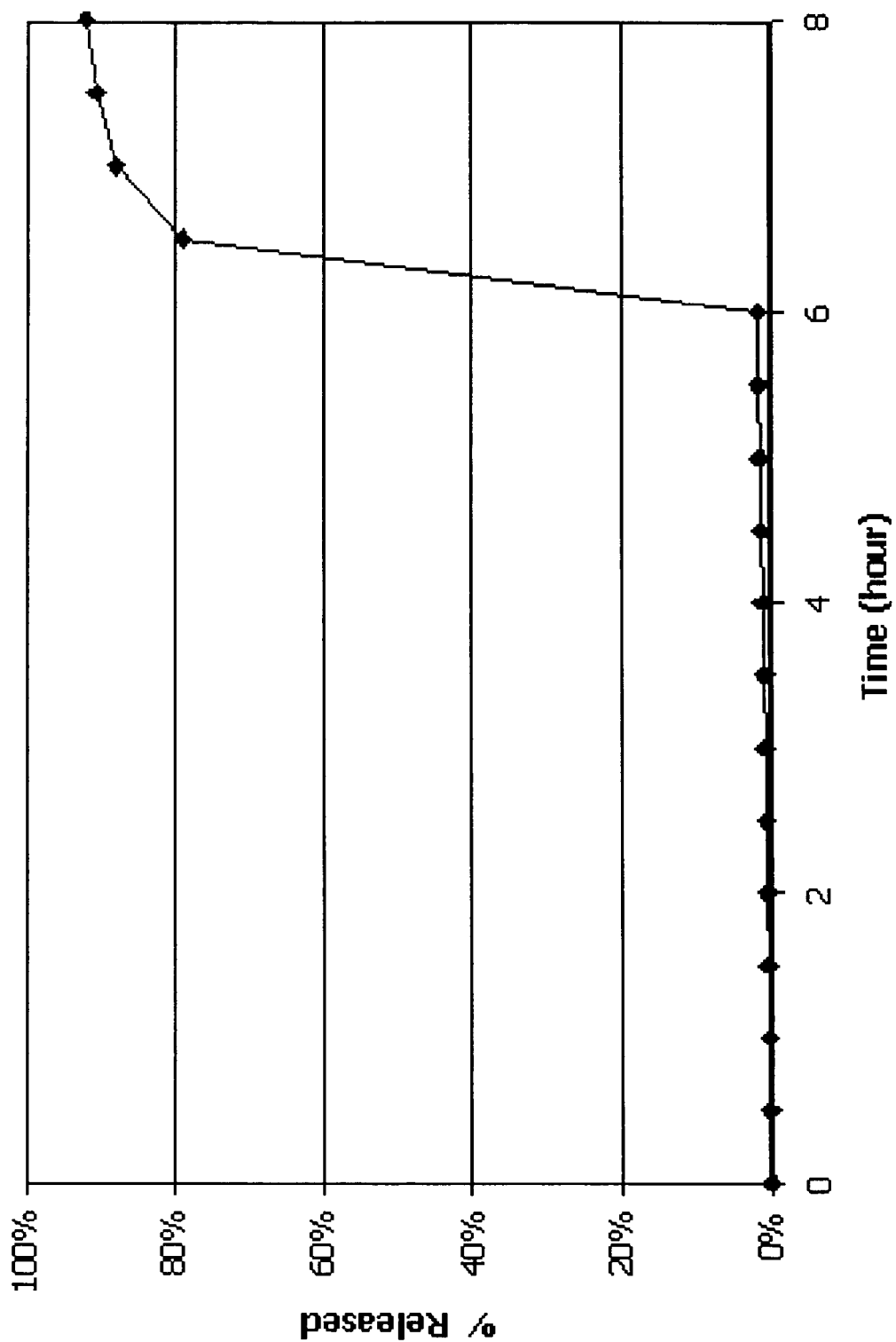

The release profiles for the active ingredients contained in the dosage forms of Examples 1-2 are shown in FIGS. 1 and 2, which depict the percent release of active ingredient versus hours for the dosage forms of Example 1 and Example 2 respectively.

All curves were derived using the following dissolution apparatus: USP Type II apparatus (paddles, 50 RPM). Media: pH 6.8 phosphate buffer at 37° C. Time points: Samples were removed at 0.5, 1, 1.5, 2, 2.5, 3, 3.5, 4, 4.5, 5, 5.5, 6, 6.5, 7, 7.5, and 8 hours to be analyzed for ibuprofen. Dissolution samples were analyzed for ibuprofen versus a standard prepared at the theoretical concentration for 100% released of the compound. Samples were assayed spectrophotometrically using a Cary 50 UV-Visible spectrophotometer at 254 nm for ibuprofen content.

We claim:

1. A delayed burst release dosage form comprising a compressed core in the form of a tablet or capsule and an overcoated shell portion, said overcoated shell portion surrounding said core,
    wherein said overcoated shell portion comprises a composition comprising 40 to 95 weight percent of a high molecular weight water soluble polymer having a weight average molecular weight from about 140,000 to about 1,150,000 and a cloud point from about 20 to about 90° C.,
    5 to 25 weight percent carrageenan, and
    0.5 to 5 weight percent gellan gum,
    wherein said core comprises a pharmaceutical active ingredient selected from analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof,
    wherein said overcoated shell portion provides for a delayed release of the active ingredient from the dosage form such that release of the pharmaceutical active ingredient is delayed for a predetermined time after ingestion and wherein after said predetermined time said pharmaceutical active ingredient is promptly released.

2. The dosage form of claim 1, wherein the water soluble polymer is selected from the group consisting of hydroxypropylmethyl cellulose, hydroxypropyl cellulose, methyl cellulose, polyvinyl alcohol, and mixtures thereof.

3. The dosage form of claim 2, wherein the water soluble polymer comprises hydroxypropyl methylcellulose having a viscosity from about 80 to about 120,000 mPa s in 2% aqueous solution.

4. The dosage form of claim 1, further comprising an inorganic cation.

5. The dosage form of claim 4, wherein the inorganic cation is selected from the group consisting of potassium cations, calcium cations, and mixtures thereof.

6. The dosage form of claim 1, further comprising a lubricant.

7. The dosage form of claim 6, wherein the lubricant is glyceryl monostearate.

8. The dosage form of claim 1 wherein the shell portion is in solid form and has a pore volume in the pore diameter range of 0.5 to 5.0 microns of less than about 0.02 cc/g.

9. The dosage form according to claim 1, wherein said predetermined time is at least four hours, wherein less than 20% of the pharmaceutical active ingredient is released prior to said predetermined time.

10. The dosage form according to claim 1, wherein said core and said shell are prepared by thermal setting molding or thermal cycle molding.

11. The dosage form according to claim 8, wherein the shell portion is in solid form and has a pore volume in the pore diameter range of 0.5 to 5.0 microns of less than about 0.01 cc/g.

12. The dosage form according to claim 8, wherein the shell portion is in solid form and has a pore volume in the pore diameter range of 0.5 to 5.0 microns less than about 0.005 cc/g.

* * * * *